United States Patent [19]
Creuly et al.

[11] Patent Number: 4,957,862
[45] Date of Patent: Sep. 18, 1990

[54] MICROBIOLOGICAL PROCESS FOR THE PREPARATION OF METHYL KETONES

[75] Inventors: Catherine Creuly, Lempdes; Jean-Bernard Gros, Chamalieres; Christian Larroche, Clermont-Ferrand, all of France

[73] Assignee: Sanofi, Paris, France

[21] Appl. No.: 482,710

[22] Filed: Feb. 21, 1990

[30] Foreign Application Priority Data

Feb. 27, 1989 [FR] France .................. 89 02524

[51] Int. Cl.$^5$ .................. A23L 1/221; C12P 7/26; C12R 1/80; C12R 1/685
[52] U.S. Cl. .................. 435/148; 426/534; 426/650; 435/917; 435/918; 435/933; 435/945
[58] Field of Search .............. 435/148, 917, 918, 933, 435/945; 426/534, 650

[56] References Cited

U.S. PATENT DOCUMENTS 3,904,780  9/1975  Yamamoto et al. .................. 426/534
4,832,964  5/1989  Pratt .................. 426/33

FOREIGN PATENT DOCUMENTS 0054987  6/1982  European Pat. Off. .
0068594  1/1983  European Pat. Off. .
2617501  7/1987  France .
57-141295  9/1982  Japan .................. 435/148

OTHER PUBLICATIONS

Enzyme Microb. Technol., 1989, 11, Feb., 106–112.
Derwent Abstract 86–150906/24 Hoeghst A. G. Deger et al DE 3444282 (6–1986).
Biotech Derwent Abs. 86–02378 Kanisawa NSKGAX, J. Jpn. Soc. Food Sci Tech (1985) 32, 11, 707–9787–90.
Biotech Derwent Abs. 89–07740 Larroche et al. Eur. Congrs. Biotech. 1987 vol. 2 197–200.
Biotech Derwents Abs 88–03455 DD–248501 (8–1987).

*Primary Examiner*—Herbert J. Lilling
*Attorney, Agent, or Firm*—Bacon & Thomas

[57] ABSTRACT

The invention deals with a process for the preparation of $C_5$ to $C_{10}$ aliphatic methyl ketones by the aerobic biotransformation of $C_6$ to $C_{11}$ fatty acids with spores of filamentous fungi of the genus Amastigomycota. The process is carried out in an inert organic solvent with a partition coefficient between water and octane superior to 4, advantageously in a $C_8$ to $C_{20}$ aliphatic hydrocarbon or a mixture of such hydrocarbons, containing at most 20% of water.

The obtained methyl ketones may be used to strengthen taste or a flavoring agents.

14 Claims, No Drawings

MICROBIOLOGICAL PROCESS FOR THE PREPARATION OF METHYL KETONES

The present invention relates to a process for the preparation of methyl ketones by the incubation of carboxylic acids with fungal spores in an organic medium.

The aromatic molecules characteristic of the taste of "blue" cheeses include methyl ketones, especially heptan-2-one and nonan-2-one, which result in nature from β-oxidation followed by decarboxylation of the fatty acids with one carbon more by enzymes present in the spores and the mycelium of the fungus *Penicillium roquefortii*. Reference may be made, for example, to the review by John E. Kinsella and Dong H. Hwang, published in Critical Reviews in Food Science and Nutrition 8 (2) p. 191–228 (1976), which summarizes the numerous studies published on this subject and mentions a number of in vitro fermentation studies.

These compounds can be obtained by the action of these enzymes on milk fats, said enzymes being present to various extents in different class III filamentous fungi, including the Amastigomycota, and in particular in the Deuteromycotina, according to the classification established by Botton and Coll in "Moisissures utiles et nuisibles" ("Useful and harmful molds"), published by Masson—Paris FR (1985), including *Penicillium roquefortii*, *Penicillium caseicolum*, *Aspergillus oryzae*, *Aspergillus niger* and *Trichoderma koningii*. These ketones are used to strengthen the taste of unripe cheeses or to give various foods, such as sauces, biscuits and dairy products, a "blue" flavor; consumers greatly value these products and it was desirable to reduce their manufacturing cost in order to be able to broaden their distribution. To do this, it was necessary in particular to improve the biotransformation of the fatty acids into the flavor-imparting methyl ketones, whether at the spore production stage or during the production of the flavor-imparting compounds under the influence of the spores. A variety of studies were carried out to this end and C. Larroche et al. described an improved process for the production of *Penicillium roquefortii* spores by fermentation in a solid medium, on buckwheat seeds, in Appl. Microbiol. Biotechnol. 28 85–92 (1988), and reported their study of the influence of the Penicillium strain and various activators on the production of heptan-2-one from octanoic acid, in an aqueous medium, in J. of Ind. Microbiology 3 p. 1–8 (1988), and with immobilized spores in Enzyme Microbiotechnology 11 (2) p. 106–112 (1989).

It has now been found that it is possible very substantially to increase the concentration of fatty acid in the medium and the productivity of the spores in respect of methyl ketones, and to reduce the losses of volatile methyl ketones, by performing the biotransformation in an organic medium, either with immobilized spores or with free spores.

There are not many examples of biotransformation in an organic medium, despite the potential advantages, numerous biocatalysts being inactivated or denatured by the customary organic solvents; it is therefore surprising to find that the spores of *Penicillium roquefortii* and the other filamentous fungi mentioned above perform the biotransformation of fatty acids into methyl ketones in the organic media of the invention with results superior to those obtained in a purely aqueous medium.

Thus the present invention relates to a process for the preparation of $C_5$ to $C_{10}$ aliphatic methyl ketones by the transformation of a $C_6$ to $C_{11}$ fatty acid or a suitable mixture of such fatty acids, in an aerobic organic medium, under the action of free or immobilized fungal spores, for example immobilized in a matrix of cross-linked gelatin or alginate.

The organic solvent used as the reaction medium must obviously be inert, but also must only have a weak polarity; thus it was found that, in the case of octanoic acid, the reaction did not take place in ethyl ether or toluene and that, in hexane or methylcyclohexane, the results were quite similar to those obtained in an aqueous medium, whereas $C_8$ to $C_{20}$ aliphatic hydrocarbons, i.e. the liquid paraffinic, isoparaffinic and cycloparaffinic hydrocarbons, either pure or as mixtures, make it possible to obtain higher biotransformation yields than those obtained in aqueous media. Also, to carry out the process of the invention, a practically apolar solvent, i.e. a solvent with a high partition coefficient P between water and octane, is used as the reaction medium. It is considered here that P is high if log P, determined by the method of R. F. Rekker described in Eur. J. Med. Chem. 14 479 (1979), is greater than 4 and preferably between 7 and 9.

Accordingly the organic solvent used in the process of the invention is advantageously chosen among the $C_8$ to $C_{20}$ aliphatic hydrocarbons or their mixtures, which show the above described characteristics. A mixture of $C_{13}$ to $C_{16}$ paraffinic hydrocarbons may more particularly be used. Said solvent as explained hereafter contains at most 20% of water.

The spores used in the process of the invention are obtained by conventional fermentation processes in the solid or liquid phase. After fermentation of the fungus in a solid medium, the complete fermentation medium can be used as the biocatalyst, for example when the fermentation has taken place on buckwheat seeds; it is also possible to separate the external spores from the medium, in conventional manner, by suspending the medium (when fermentation has ended) in water in the presence of a surfactant such as Tween 80, before separating the spore-containing liquid from the solids by filtration, after which the spores may be isolated, if desired, by centrifugation.

The isolated spores can be introduced as such into the biotransformation medium or after immobilization in a matrix consisting of alginate beads which have been consolidated, after inclusion, by the action of polyethyleneimine and glutaraldehyde, as described by S. Birnbaum in Biotechnol. Lett. 3 p. 393–400 (1982), or by coating with a polymer, such as an acrylic copolymer, according to the process described by W. Hartmeier and A. Heinrichs in Biotechnol. Lett. 8 p. 567–572 (1986) for the immobilization of mixtures of microbial cells and enzymes; the spores can also be immobilized in microbeads of gelatin crosslinked with an oxidized polysaccharide, as described in European patent application A-308 330, or by any other method known to those skilled in the art.

If the spores are not used quickly, they are stored frozen at about $-15°$ C.

It is obvious that the biotransformation medium is not anhydrous since a certain amount of water is introduced with the spores, whether they have been isolated or immobilized, and it has been found that if the volume of water represents only a few % of the volume of the organic medium according to the invention, the results of the biotransformation are markedly superior to those obtained in a purely aqueous medium. Nevertheless, as it is preferable for a certain amount of water to be present throughout the biotransformation, and in order to prevent dehydration due to stripping of the water by the stream of air required for these aerobic reactions, the biotransformation can be started with a volume of water representing up to 20% of the volume of the organic solvent; if only about 5% of water is initially introduced into the medium, it is preferred to compensate the losses by introducing moisture-laden air.

The acid to be transformed is introduced into the spore-containing reaction medium in successive steps or continuously: the optimum concentrations of acid in the reaction medium depend on the nature of the acid involved and that of the solvent and the fungus, but are always considerably higher than those which are permissible when the process is carried out in a purely aqueous medium; this is another advantage of the invention.

Thus, in the case of octanoic acid and an isoparaffinic solvent with a log P of about 7, the bio-transformation is not inhibited by an acid concentration in the medium of as much as 300 mmol per liter of solvent, and for approximately $10^{11}$ *Penicillium roquefortii* spores immobilized in crosslinked alginate, suspended in a $C_{13}$ to $C_{16}$ paraffinic solvent, the yield is about 80% for a concentration adjusted to 100 mM.

The biotransformation temperature depends on the fungus used and those skilled in the art will be able to fix it after a few preliminary experiments; in general, it is below 30° C. and preferably between 25° C. and 30° C.

Examples of how to carry out the process of the invention are described below.

EXAMPLE 1

(a) Preparation of the spores 300 g of buckwheat seeds, boiled in a water bath at 100° C. for 30 min in water containing 350 mg/l of chloramphenicol, drained and then sterilized in an autoclave for 20 min at 120° C., are inoculated at a rate of $10^5$ to $10^6$ spores, originating from *Penicillium roquefortii* ATCC 64 383 strain, per gram of dry matter.

These seeds are placed in previously sterilized, aerated fermenters to give about $5 \times 10^9$ spores/g of solids in 12 to 15 days. The spores outside the seeds are then extracted by agitation at room temperature in a 0.05% aqueous solution of Tween 80 ®, at a rate of 5 to 10 ml of solution per gram of fermentation medium, and the seeds are filtered off. A concentrated solution of free spores is obtained after decantation or, for a more concentrated medium, after centrifugation of this filtrate.

To store the spores for more than 24 hours, they can be frozen at a temperature below $-15°$ C., either in the aqueous isolation medium or in their fermentation medium, in which case the spores will have to be rehydrated by being kept in suspension in water at 5° C. for at least 10 h before use.

(b) Immobilization of the spores in alginate

A suspension of $8 \times 10^{10}$ isolated spores in 10 ml of water is introduced into 120 ml of a 2% (w/v) solution of sodium alginate which has first been homogenized by violent agitation and then deaerated under vacuum.

By means of a peristaltic pump, the mixture is then passed through needles of diameter 0.6 mm to form droplets, which are hardened on falling into 200 ml of an emulsion consisting of an aqueous solution of a mixture of $CaCl_2$ and an acrylate/methacrylate copolymer with a molecular weight of about 150,000, such as Eudragit RL100 ® marketed by Röhm Pharma (FRG); the emulsion was prepared by introducing one volume of a 1% (w/v) suspension of Eudragit in distilled water, which has first been heated for 20 min at 121° C., into one volume of a 0.1M aqueous solution of $CaCl_2$ at 18° C.

30 min after the addition of the alginate droplets has ended, the suspension of beads is agitated and then left to stand for 15 h at 5° C.; the supernatant liquid is then removed and the beads, which have a diameter of about 3 mm, are rinsed twice with sterile distilled water containing 350 mg/l of chloramphenicol. This gives 130 g of beads containing about $8 \times 10^{10}$ spores.

(c) Biotransformation

The wet beads prepared according to (b) are introduced into 400 ml of an isoparaffinic solvent marketed by Total Solvants (France) under the reference IP 230 OS, which consists of a mixture of saturated $C_{13}$ to $C_{16}$ hydrocarbons with boiling points above 230° C. and a viscosity, measured according to standard NF T 60–100, of 4.10 mm$^2$/s at 20° C. The 750 ml reactor is agitated by a blade turbine rotating at 600 rpm and air is introduced into the medium at a rate of 1.2 l per hour; the system is kept at 27° C. by the circulation of a liquid in the jacket of the reactor.

7 g (100 mM) of octanoic acid are introduced at the start of the biotransformation and the concentration of octanoic acid in the reactor is then readjusted to its initial value (100 mM), about every 12 hours, by addition of the required amount of acid. After 212 h, the amount of acid transformed is 111 g and, after the catalyst has been filtered off, 70 g of heptan-2-one are isolated from the solvent by distillation at 79° C. under 9 kPa. Part of the ketone formed has been stripped away by the circulating air and approximately a further 11 g of ketone are recovered if a trap is installed at the reactor outlet.

EXAMPLE 2

The catalyst is prepared as in Example 1 and 50 g of beads containing $2 \times 10^8$ spores per gram are introduced into 150 ml of the same solvent as above, in an agitated Erlenmeyer flask kept at 27° C., with surface aeration only. 28 hours after the addition of 2.4 g of octanoic acid, it is found that all the acid has been transformed; the yield of heptan-2-one isolated is 80%.

EXAMPLE 3

The catalyst is prepared as in Example 1 and 50 g of beads containing $2 \times 10^8$ spores per gram are introduced into 150 ml of hexadecane in an agitated reactor kept at 27° C., with surface aeration only. 2.4 g (100 mM) of octanoic acid are introduced at the start of the biotransformation and the concentration of octanoic acid in the reactor is then readjusted to 100 mM about every 24 hours.

After 160 h, the amount of acid transformed is 9.6 g and 6.5 g of heptan-2-one are isolated by distillation of the solvent from the reaction medium.

EXAMPLE 4

By operating under the same conditions as in Example 1 with $C_{10}$ capric acid at an initial concentration of 100 mM, the mean degree of transformation to nonanone is 70% and the productivity—i.e. the concentration of acid transformed—is 0.71 mmol per hour.

EXAMPLE 5

By operating under the same conditions as in Example 1 with $C_6$ caproic acid at an initial concentration of 50 mM, the average degree of transformation is 70% and 8 g/l of pentan-2-one are obtained in 5 days.

EXAMPLE 6

180 g of sporulated buckwheat seeds, obtained as described in Example 1 and containing $1.5 \times 10^9$ spores per gram of dry matter, are introduced into a 1.5 liter reactor; 250 ml of a 0.05% (w/v) aqueous solution of Tween 80 ® and 1 liter of the paraffinic solvent IP 230 OS are added in succession; during the biotransformation, the reaction medium is to be kept at 27° C., with agitation, and aerated at a rate of 1 liter per hour by means of an air bubbling system.

16.6 g (115 mM) of octanoic acid are then added and further octanoic acid is added every eight hours to replace that which has been consumed. After 39 hours, the buckwheat seeds are separated from the reaction medium by filtration on a sieve of mesh 0.8 mm and the biotransformation is continued. After 111 hours, 127 g of acid have been transformed and 92 g of heptan-2-one are isolated by distillation at 79° C. under 9 kPa.

This operation can also be carried out by introducing the octanoic acid continuously into the medium by means of a pump; in the case where the concentration of acid is fixed at 70 mM, the results are identical to those of the batch procedure.

EXAMPLE 7

*Penicillium roquefortii* is cultured on buckwheat seeds as described in Example 1. When culture is complete, 30 g of seeds are introduced into 150 ml of a 0.05% (w/v) aqueous solution of Tween 80 ® and, after gentle agitation for a few minutes to detach the external spores, the medium is filtered on a sieve of mesh 0.8 mm and the filtrate is centrifuged at 4200 rpm to give a few milliliters of residue containing $45 \times 10^9$ spores.

This residue which has been separated off is suspended in 50 ml of a 0.05% aqueous solution of Tween 80 ®, and 200 ml of the solvent IP 230 OS are added; the resulting mixture is placed in a flask at 27° C. and a slow stream of air is introduced near the surface of the mixture. 3.3 g (100 mM) of octanoic acid are then introduced and the concentration of acid is readjusted to 100 mM every 12 hours; after 155 hours, 13.8 g of acid have been transformed and 8.8 g of heptan-2-one can be isolated from the reaction medium by distillation.

EXAMPLE 8

*Penicillium roquefortii* spores are obtained by solid fermentation as in Example 1, but are used in the presence of the buckwheat seeds; $12 \times 10^{11}$ spores, 90 ml of a 0.05% aqueous solution of Tween ® and 600 ml of the solvent IP 230 OS are then introduced into the reactor. Caproic acid is introduced into the medium at an initial concentration of 100 mM and the amount required to readjust the concentration to this value is then introduced every 12 h; the average degree of transformation is 70% for an acid consumption of 1.67 mM/h. After 300 h, 51 g/l of nonan-2-one are obtained by distillation.

EXAMPLE 9

By operating under the same conditions as in Example 8 with $C_6$ caproic acid at a concentration of 50 mM, 17 g/l of pentan-2-one are obtained in 250 h.

EXAMPLE 10

Spores of *Aspergillus oryzae* ATCC 1861 are obtained from cultures on a gelose medium in Petri dishes. The contents of each dish are suspended in water containing 0.05% of Tween ® so as to extract the spores from the gelose matrix. $3 \times 10^9$ spores suspended in 22.5 ml of water are then introduced into an Erlenmeyer flask containing 150 ml of the paraffinic solvent IP 230 OS and 20 mM octanoic acid. The acid has been totally consumed after 24 hours.

EXAMPLES 11 to 14

The biotransformation of octanoic acid is performed with other fungi by applying the process of Example 10. The results are shown in Table 1.

TABLE I

| Species | Reference of the strain | Transformation ended after |
| --- | --- | --- |
| Penicillium roquefortii | ATCC 6989 | 10 h |
| Penicillium caseicolum | ATCC 123 | 30 h |
| Aspergillus niger | ATCC 9142 | 48 h |
| Trichoderma koningii | DSM 63060 | 30 h |

COMPARATIVE EXAMPLE

Biotransformation in an aqueous medium 115 g of beads of immobilized spores, prepared as in Example 1, are introduced into 350 ml of water containing 350 mg/l of chloramphenicol to prevent bacterial contamination, 0.2 mg/l of ethanol as a biotransformation activator and 0.005 mol per liter of calcium chloride to consolidate the alginate beads. The medium is aerated by air blowing as soon as the latency phase has ended, and is agitated as in Example 1.

The air leaving the reactor is laden with heptan-2-one, at least part of which can be retained by bubbling into toluene. After the addition of 0.11 g of octanoic acid, the pH is adjusted to 6.5 with aqueous NaOH and kept at this value for 166 hours by the addition of octanoic acid. 8 g of acid are transformed under these conditions; the latency phase lasts about 4 hours.

What is claimed is:

1. A process for the preparation of $C_5$ to $C_{10}$ aliphatic methyl ketones by the aerobic biotransformation of $C_6$ to $C_{11}$ fatty acids with spores of filamentous fungi of the genus Amastigomycota, wherein the reaction medium is a $C_8$ to $C_{20}$ aliphatic hydrocarbon or a mixture of such hydrocarbons containing at most 20% of water.

2. A process according to claim 1, wherein the fungus is selected from the group consisting in *Penicillium roquefortii*, *Penicillium caseicolum*, *Aspergillus oryzae*, *Aspergillus niger* and *Trichoderma koningii*.

3. A process according to claim 1, wherein the solvent is a mixture of $C_{13}$ to $C_{16}$ paraffinic hydrocarbons.

4. A process according to claim 2, wherein the solvent is a mixture of $C_{13}$ to $C_{16}$ paraffinic hydrocarbons.

5. A process according to claim 1, wherein the spores are free.

6. A process according to claim 1, wherein the spores are used in their solid production medium.

7. A process according to claim 1, wherein the spores are immobilized in a porous matrix.

8. A process according to claim 1, wherein the fungus is *Penicillium roquefortii*.

9. A process according to claim 2, wherein the fungus is *Penicillium roquefortii*.

10. A process according to claim 1, wherein the fatty acid is selected from the group consisting in octanoic acid, capric acid, caproic acid.

11. A process according to claim 1, wherein the fatty acid is octanoic acid.

12. A process according to claim 2, wherein the fatty acid is octanoic acid.

13. A process according to claim 3, wherein the fatty acid is octanoic acid.

14. A process according to claim 8, wherein the fatty acid is octanoic acid.

* * * * *